United States Patent [19]
Thomas

[11] Patent Number: 5,900,068
[45] Date of Patent: May 4, 1999

[54] CLEANING OR APPLICATOR DEVICE

[75] Inventor: George H. Thomas, Dayton, Ohio

[73] Assignee: LeGrand Tour Group, Inc., Fairborn, Ohio

[21] Appl. No.: 08/748,285

[22] Filed: Nov. 13, 1996

[51] Int. Cl.[6] ..................................................... A47L 13/28
[52] U.S. Cl. ............................................... 134/6; 15/209.1
[58] Field of Search ................................ 15/209.1, 210.1, 15/229.11, 229.14, 244.1, 244.4; 134/6, 34

[56] References Cited

U.S. PATENT DOCUMENTS

| | | | |
|---|---|---|---|
| 671,130 | 4/1901 | Darden . | |
| 1,146,359 | 7/1915 | Smith | 15/210.1 |
| 1,519,577 | 12/1924 | Easton, Jr. . | |
| 2,761,166 | 9/1956 | Connolly | 15/210.1 |
| 2,964,772 | 12/1960 | Crawford | 15/244.1 |
| 3,142,855 | 8/1964 | Gilchrist | 15/210.1 |
| 3,784,998 | 1/1974 | Jones | 15/209.1 |
| 4,199,835 | 4/1980 | Heyer et al. . | |
| 5,140,785 | 8/1992 | Eleouet . | |
| 5,230,119 | 7/1993 | Woods et al. | 15/209.1 |

FOREIGN PATENT DOCUMENTS

| | | | |
|---|---|---|---|
| 1434159 | 2/1966 | France | 15/244.1 |
| 1029136 | 4/1958 | Germany | 15/244.1 |

*Primary Examiner*—Terrence R. Till
*Attorney, Agent, or Firm*—Maginot, Addison & Moore

[57] ABSTRACT

A cleaning device includes a barrier having (1) a central axis, (2) a first barrier segment extending from the central axis, (3) a second barrier segment extending from the central axis, and (4) a third barrier segment extending from the central axis. The cleaning device also includes a first cleaning layer having a first layer front side and a first layer back side, the first layer back side being attached directly to the first barrier segment and the second barrier segment. The cleaning device further includes a second cleaning layer having a second layer front side and a second layer back side, the second layer back side being attached directly to the second barrier segment and the third barrier segment. In addition, the cleaning device includes a third cleaning layer having a third layer front side and a third layer back side, the third layer back side being attached directly to the first barrier segment. The cleaning device also includes a cleaning agent impregnated within the first cleaning layer. A method of utilizing the cleaning device is also disclosed.

20 Claims, 5 Drawing Sheets

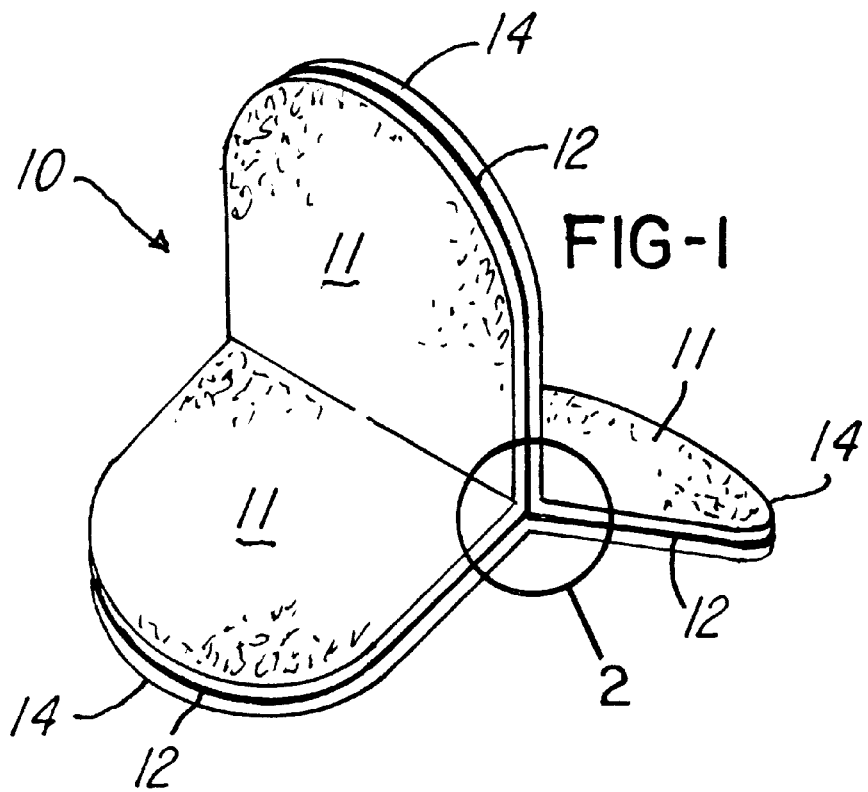
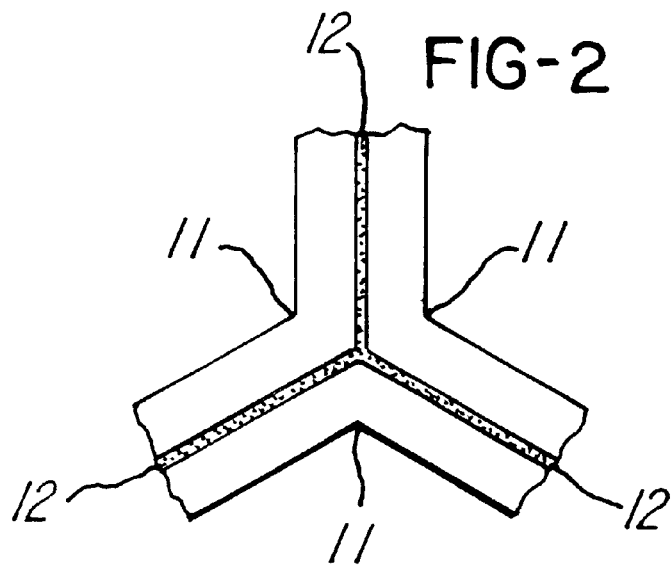

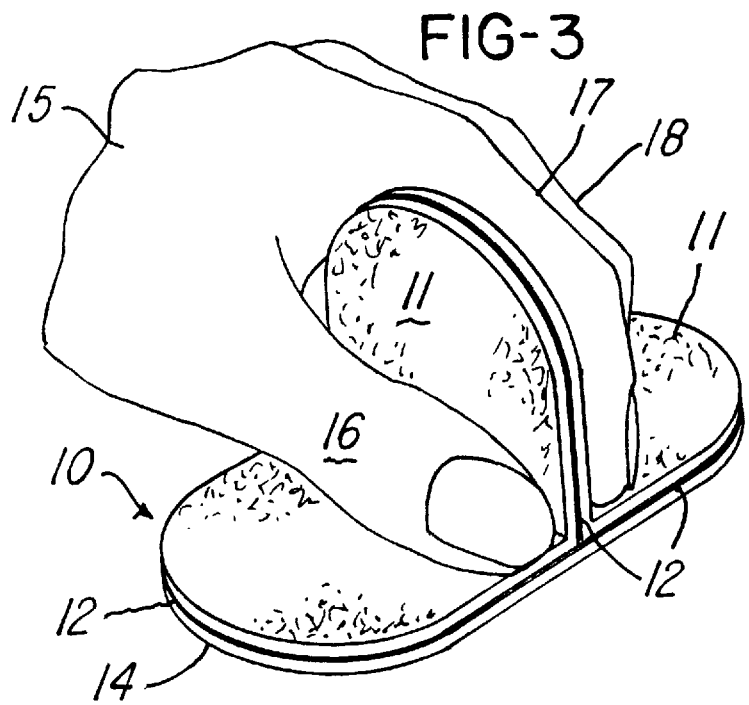
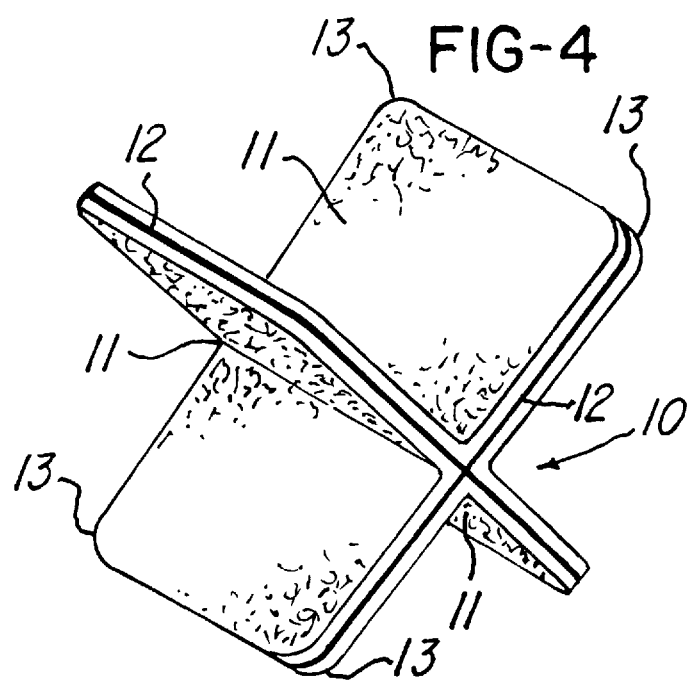

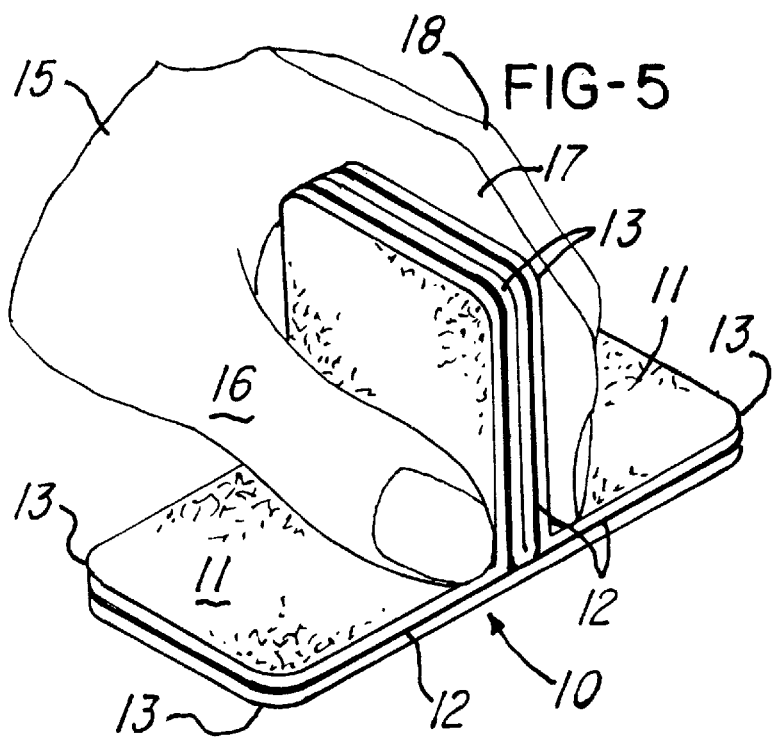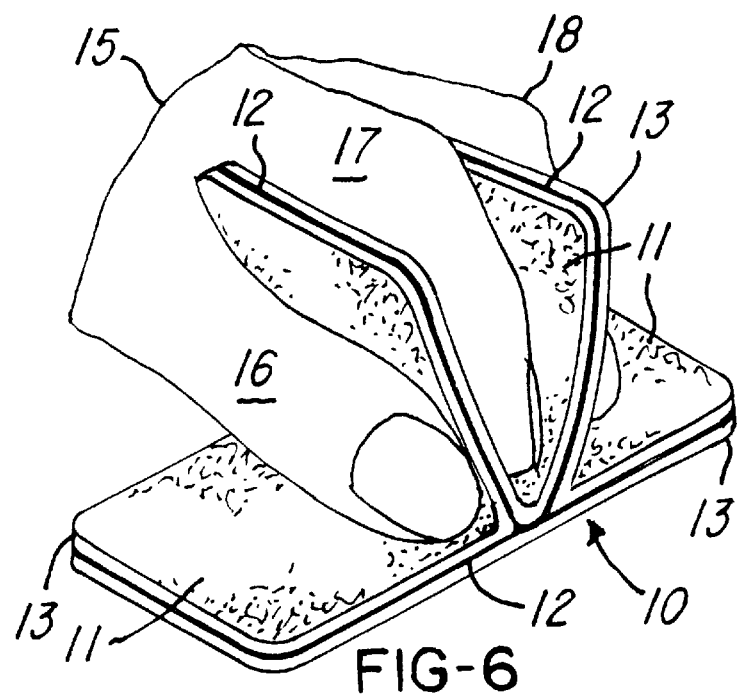

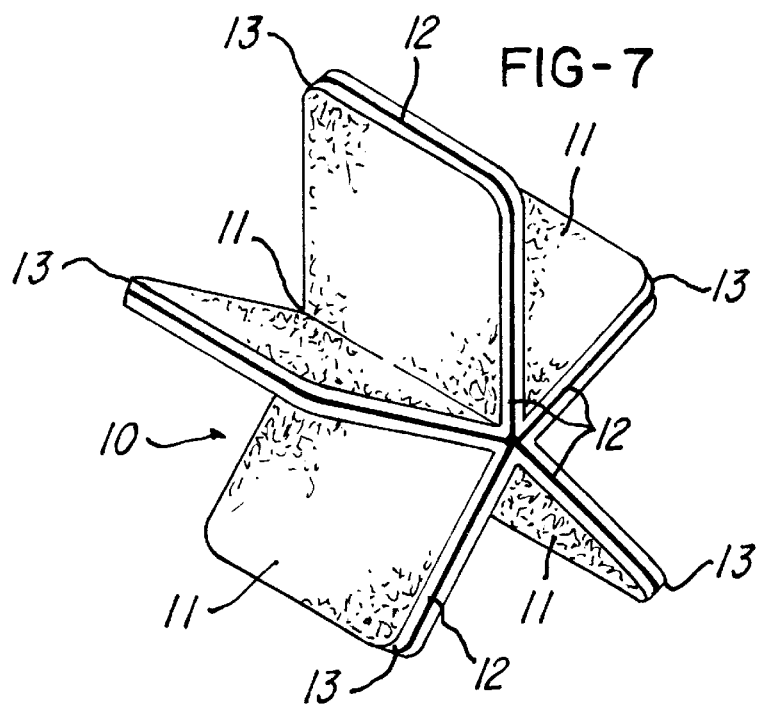
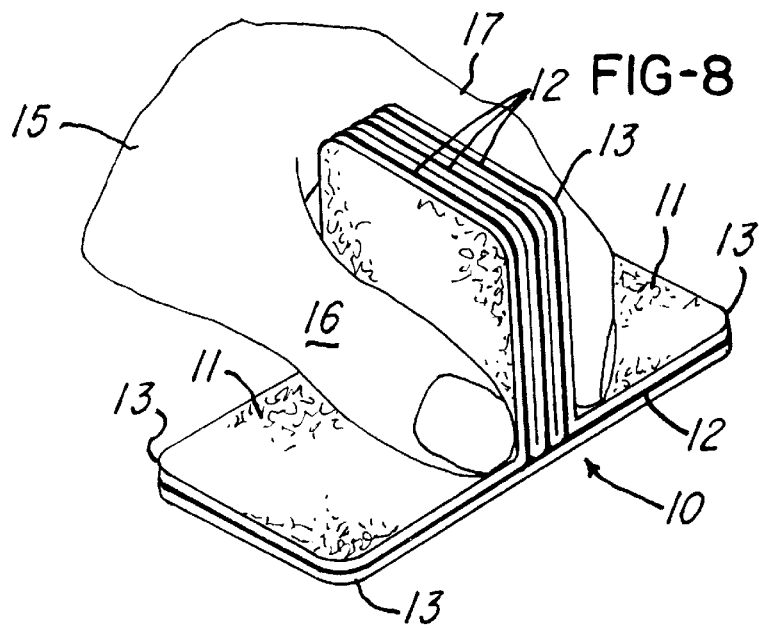

… (5,900,068)

CLEANING OR APPLICATOR DEVICE

BRIEF DESCRIPTION OF THE INVENTION

The present invention is directed to a cleaning and/or applicator device which is hand held by the fingers, contains at least three and usually from three to six separate cleaning/applicator layers, the exterior of at least one of which is absorbent, and the interior surfaces of each of which are joined by a non-absorbent barrier layer. The outer extent of these layers can have edges which are generally rounded; or these layers can have a generally elliptical configuration.

BACKGROUND OF THE INVENTION AND PRIOR ART

In the varied fields of cleaning, cosmetics, and related endeavors, it has been customary to utilize separate applicator devices such as washcloths, towels, powder puffs, cleaning cloths, etc., for the application and removal, respectively, of cleaning solutions, polishing waxes and liquids, powder, and make-up which can be in the form of a liquid, wax, or powder-containing material, in the various fields and utilities previously mentioned. This is not only costly but duplicative in that a plurality of such media has been previously employed for the respective application and removal functions mentioned. The present invention enables the aforementioned tasks to be completed using a single applicator device which is grasped by the fingers of the hand or in desired situations the fingers of both hands.

U.S. Pat. No. 1,146,359 issued Jul. 13, 1915 to W. D. Smith is directed to sandpaper permitting the utilization of practically the entire surface of the sandpaper until such time as that shall become too work for further use. At that time the sandpaper is discarded. This sandpaper structure is referred to by the patentee as trifoliate made of three similar leaves, (2), (3), and (4), each being in rectangular form and all branching from a common central line.

U.S. Pat. No. 671,130 issued Apr. 2, 1901 to N. J. Darden is directed to a pencil sharpener comprised of a suitable tablet having an abrasive surface(s), viz., the inner or upper side of tablet (A), or surfaces (C) and (D) and a protecting shield (E). The protecting shield is composed of felt or other suitable flexible material and the flexibility of the tablet enables it to be bent around the edge of a desk to present a rounded abrasive surface to the point or end of a pencil to facilitate sharpening the pencil and also permitting the tablet to be folded into a V-shape so that when the end of a pencil is inserted in the fold and rapidly turned, the desired point will be produced at the end of the pencil.

U.S. Pat. No. 5,140,785 issued on Aug. 25, 1992 to Bernard Eleouet is directed to a multifunctional composite block for manual treatment of surfaces, the block including several different pads (1) attached to a flexible connecting sheet (2) that permits superimposing the pads in at least two different configurations so that the surfaces of different pads define the outer surface of the block.

U.S. Pat. No. 1,519,577 issued on Dec. 16, 1924 to H. P. Easton, Jr. is directed to a cleaning and abrading device apparently of the steel wool or variety that serves as a scouring pad. The Easton, Jr. scouring pad is comprised of a back (10) of textile fabric flexible in all directions, a mass (11) of metallic steel wool applied to the back and stitched thereto at a plurality of points (15) and wherein one end of the back is extended to form a handle (16) and flexible cloth strips (14) extend longitudinally and transversely over the face of the metallic wool with stitches (15) extending through the flexible strips and the metallic wool and holding the flexible strips to the back. The ends of the strips are stitched to the back.

U.S. Pat. No. 4,199,835 issued to Raymond F. Heyer, et al, on Apr. 29, 1980 is directed to a scouring pad (10) in the shape of a ball comprised of a plurality of radially slit, regular-shaped, planar segments (11) of conformable, lofty, low-density non-woven abrasive product fastened together under compression at their centers (12) with fastening means (13). The segments are slit from the outer edge toward the center to provide radially disposed, equally spaced slits (15) which define readily aligned lobes (14), the total array of which defines the ball shape.

It will be observed that the aforementioned prior art references lack the variety of utility, the ability to be cleaned and re-used, and the ease of use as well as the structural requirements of the present invention.

BRIEF DESCRIPTION OF THE DRAWINGS

FIG. 1 is a perspective side view of a cleaning pad/applicator device of this invention having three separate cleaning/applicator layers.

FIG. 2 is a partial cross-sectional view of the central portion of the device of FIG. 1 from the perspective (2) of FIG. 1.

FIG. 3 is a perspective side view of the cleaning pad/applicator device of FIG. 1 in use being held by the fingers of one hand.

FIG. 4 is a perspective view of a cleaning/applicator device in accordance with this invention having four separate cleaning/applicator layers.

FIG. 5 is a perspective side view of the cleaning/applicator device of FIG. 4 in use being held by the fingers of one hand in a position with a thumb on one side and the remaining fingers on the other side and with two separate layers there between.

FIG. 6 is a perspective side view of a cleaning/applicator device of a FIG. 4 in use being held by the fingers of one hand in a position with a thumb on one side, the index finger in the middle and the remaining fingers on the other side presenting a triple "V"-shaped configuration for three of the four separate cleaning/applicator layers.

FIG. 7 is a perspective side view of a cleaning/applicator device in accordance with FIG. 7 in use with the fingers positioned in accordance with the arrangement shown in FIG. 5 only with three separate cleaning/applicator layers between them.

Figure 9:
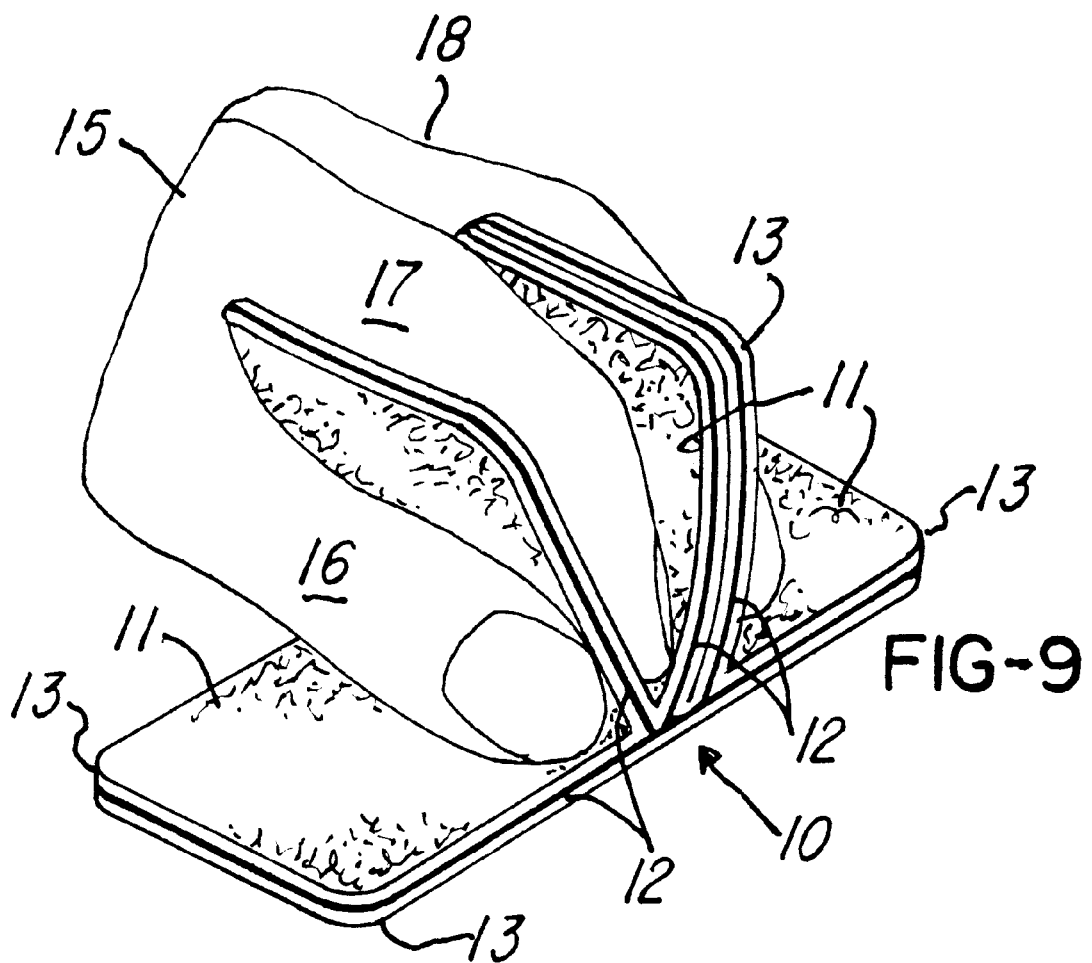
FIG. 9 is a perspective side view of a cleaning/applicator device as in FIG. 7 in use with the fingers arranged in a position similar to that shown in FIG. 6 only having a double thickness of cleaning/applicator layers between the index and remaining fingers.

The embodiment which has six separate layers (not shown) is quite similar to FIGS. 7, 8 and 9 only having the appearance of a hexagonal star rather than the pentagonal star of FIG. 7, for example: This embodiment as well can be of generally elliptical configuration, or can have edges which are generally rounded.

DETAILED DESCRIPTION OF THE INVENTION

The hand-held cleaning/applicator device of this invention (10, 10' 10") is illustrated in FIGS. 1 through 9. As shown in FIGS. 1 through 9, inclusive, this cleaning/applicator device has a plurality of separate cleaning/ applicator layers (11, 11', 11"), each being absorbent. These layers are joined by a non-absorbent barrier layer (12, 12' 12") such as adhesive which is resistant to migration of liquids, pastes, powder, etc., there through. The non-absorbent barrier layer 12, 12', and 12" respectively have a central axis CA (see FIG. 1), CA'(see FIG. 4), and CA" (see FIG. 7).

As noted previously, the cleaning/applicator devices of this invention can have generally rounded edges (13', 13") as shown in FIGS. 4 through 9. alternatively, the cleaning/applicator devices in accordance with this invention can have a generally elliptical configuration as is apparent from FIGS. 1 and 3 of the drawings.

As is shown in FIGS. 3, 5, 6, 8 and 9, the cleaning/applicator device of this invention can be grasped using the fingers of one hand (15, 15', 15"). In accordance with one manner of grasping a device having three separate cleaning/applicator absorbent layers,, as is shown in FIG. 3, the applicator device (10) is grasped with the thumb (16) on one side of an intermediate layer and the index finger (17) and remaining fingers (18) grasping the other side thereof.

As is shown in FIG. 5, the same arrangement of the fingers and thumb is utilized to grasp a cleaner/applicator device having four separate absorbent layers. In this case, however, there are two separate such layers grasped between the thumb (16') and the index finger (17') and remaining fingers (18').

An alternative way of arranging the fingers to grasp device (10') is that shown in FIG. 6 in which the thumb occupies the position shown in FIG. 3 and FIG. 5 but the index finger (17') grasps between two separate independent absorbent layers with the remaining fingers (18') positioned outside thereof presenting a triple "V"-shaped configuration for three of the four separate cleaning/applicator layers.

The device (10") can have five separate absorbent layers as shown in FIGS. 7 through 9. In accordance with FIG. 8 of the drawings, the arrangement of the thumb (16"), the index finger (17") and the remaining fingers (not shown in FIG. 8) is similar to that shown in FIG. 5 except that there is a triple thickness of cleaning/applicator layers positioned between the thumb and the index and remaining fingers.

The arrangement of the thumb, index finger, and remaining fingers illustrated in FIG. 9 of the drawings is similar to that shown in FIG. 6 except that in FIG. 9 there is a double thickness of separate cleaning/applicator absorbent layers between the index finger (17") and the remaining fingers (18").

The arrangement of the fingers of both hands (not shown) can in accordance with this invention be any arrangement which is comfortable to the user of a pair of the devices (10, 10', 10") and enables him or her to accomplish certain desired tasks quicker, for example the application and removal of polish, the cleaning and wiping (drying) of glass and other surfaces, etc.

The material of which the absorbent layer (11, 11', 11"), constituting the respective separate cleaning/applicator absorbent layers for device (10) is made, can be any washable, absorbent, woven or non-woven fabric, including, but not necessarily limited to, felt, cotton, wool, nylon, polyester, etc.

One or more of the separate absorbent surfaces (11, 11' 11") can be coated and/or impregnated with the desired liquid, wax, cosmetic material, or cleaning agent which is appropriate to the task being undertaken. Thus polishing liquids, creams and other compounds can be employed for polishing such materials as shoes, silver, copper, etc. When cleaning is undertaken with the device (10, 10', 10") of this invention, for example, WINDEX™ or other suitable cleaning material can be used for the cleaning of glass and other siliceous and calcareous surfaces and materials.

In accordance with a preferred embodiment of this invention, the layers (11, 11', 11") constituting the separate absorbent exterior layers are preferably machine washable or dry-cleanable, viz., made of woven and non-woven fibrous materials capable of being cleaned in a washing machine or dry cleaning machine, using a solvent or mixture thereof which will not dissolve the non-absorbent material contained in barrier layers (12, 12', 12").

It should be realized that in accordance with this invention a variety of different separate colors can be used for each separate cleaning/applicator fibrous layer of material (11, 11', 11").

The invention claimed is:

1. A cleaning device, comprising:
    a barrier having (1) a central axis, (2) a first barrier segment extending from said central axis, (3) a second barrier segment extending from said central axis, (4) a third barrier segment extending from said central axis;
    a first cleaning layer having a first layer front side and a first layer back side, said first layer back side being attached directly to said first barrier segment and said second barrier segment;
    a second cleaning layer having a second layer front side and a second layer back side, said second layer back side being attached directly to said second barrier segment and said third barrier segment;
    a third cleaning layer having a third layer front side and a third layer back side, said third layer back side being attached directly to said first barrier segment; and
    a cleaning agent impregnated within said first cleaning layer.

2. The cleaning device of claim 1, wherein:
    said cleaning agent includes a cleaning detergent which is suitable for cleaning glass.

3. The cleaning device of claim 1, wherein (1) said barrier further has a fourth barrier segment extending from said central axis, and (2) said third cleaning layer is further attached directly to said fourth barrier segment, further comprising:
    a fourth cleaning layer having a fourth layer front side and a fourth layer back side, said fourth layer back side being attached directly to said third barrier segment and said fourth barrier segment.

4. The cleaning device of claim 1, wherein (1) said barrier further has a fourth barrier segment and a fifth barrier segment each extending from said central axis, and (2) said third cleaning layer is further attached directly to said fifth barrier segment, further comprising:
    a fourth cleaning layer having a fourth layer front side and a fourth layer back side, said fourth layer back side being attached directly to said third barrier segment and said fourth barrier segment; and
    a firth cleaning layer having a fifth layer front side and a fifth layer back side, said fifth layer back side being attached directly to said fourth barrier segment and said fifth barrier segment.

5. The cleaning device of claim 1, wherein:
    said first cleaning layer, said second cleaning layer, and said third cleaning layer each includes a felt fabric.

6. The cleaning device of claim 1, wherein:
    said first cleaning layer, said second cleaning layer, and said third cleaning layer each includes a cotton fabric.

7. The cleaning device of claim 1, wherein:

said first cleaning layer, said second cleaning layer, and said third cleaning layer each includes a wool fabric.

8. The cleaning device of claim 1, wherein:

said first cleaning layer, said second cleaning layer, and said third cleaning layer each includes a nylon fabric.

9. The cleaning device of claim 1, wherein:

said first cleaning layer, said second cleaning layer, and said third cleaning layer each includes a polyester fabric.

10. A method of cleaning an object, comprising the steps of:

providing a cleaning device which includes (1) a barrier having (i) a central axis, (ii) a first barrier segment extending from said central axis, (iii) a second barrier segment extending from said central axis, (iv) a third barrier segment extending from said central axis, (2) a first cleaning layer having a first layer front side and a first layer back side, said first layer back side being attached directly to said first barrier segment and said second barrier segment, (3) a second cleaning layer having a second layer front side and a second layer back side, said second layer back side being attached directly to said second barrier segment and said third barrier segment, and (4) a third cleaning layer having a third layer front side and a third layer back side, said third layer back side being attached directly to said first barrier segment;

cleaning a surface with said cleaning device; and washing said cleaning device in a liquid bath.

11. The method of claim 10, wherein:

said washing step includes the step of washing said cleaning device in a washing machine.

12. The method of claim 10, wherein:

said first cleaning layer, said second cleaning layer, and said third cleaning layer each includes a cotton fabric.

13. The method of claim 10, wherein:

said first cleaning layer, said second cleaning layer, and said third cleaning layer each includes a wool fabric.

14. The method of claim 10, wherein:

said first cleaning layer, said second cleaning layer, and said third cleaning layer each includes a nylon fabric.

15. The method of claim 10, wherein:

said first cleaning layer, said second cleaning layer, and said third cleaning layer each includes a polyester fabric.

16. The method of claim 10, wherein said barrier further has a fourth barrier segment extending from said central axis, said third layer back side of said third cleaning layer is further attached directly to said fourth barrier segment, further comprising:

said cleaning device further includes a fourth cleaning layer having a fourth layer front side and a fourth layer back side, said fourth layer back side being attached directly to said third barrier segment and said fourth barrier segment, and said cleaning step includes the steps of (1) positioning a thumb of a user between said second barrier and said third barrier, (2) positioning a first finger of the user between said third barrier segment and said fourth barrier segment, (3) positioning a second finger of the user between said fourth barrier segment and said first barrier segment, and (4) cleaning the surface with said first cleaning layer.

17. The method of claim 10, wherein:

said cleaning device further includes a cleaning agent impregnated on said first cleaning layer, and said cleaning step includes the step of cleaning the surface with said first cleaning layer.

18. A method of cleaning, comprising the steps of:

providing a cleaning device which includes (1) a barrier having (i) a central axis, (ii) a first barrier segment extending from said central axis, (iii) a second barrier segment extending from said central axis, (iv) a third barrier segment extending from said central axis, (2) a first cleaning layer having a first layer front side and a first layer back side, said first layer back side being attached directly to said first barrier segment and said second barrier segment, (3) a second cleaning layer having a second layer front side and a second layer back side, said second layer back side being attached directly to said second barrier segment and said third barrier segment, and (4) a third cleaning layer having a third layer front side and a third layer back side, said third layer back side being attached directly to said first barrier segment; and cleaning a glass surface with said cleaning device.

19. The method of claim 18, wherein:

said first cleaning layer, said second cleaning layer, and said third cleaning layer each includes a fabric which is selected from the group consisting of a felt fabric, a cotton fabric, a wool fabric, a nylon fabric and a polyester fabric.

20. The method of claim 18, wherein said barrier further has a fourth barrier segment extending from said central axis, said third layer back side of said third cleaning layer is further attached directly to said fourth barrier segment, further comprising:

said cleaning device further includes a fourth cleaning layer having a fourth layer front side and a fourth layer back side, said fourth layer back side being attached directly to said third barrier segment and said fourth barrier segment, and said cleaning step includes the steps of (1) positioning a thumb of a user between said second barrier and said third barrier, (2) positioning a first finger of the user between said third barrier segment and said fourth barrier segment, (3) positioning a second finger of the user between said fourth barrier segment and said first barrier segment, and (4) cleaning the glass surface with said first cleaning layer.

* * * * *